US00PP16271P2

(12) United States Plant Patent
Zaias

(10) Patent No.: US PP16,271 P2
(45) Date of Patent: Feb. 21, 2006

(54) ***NEPHROLEPIS* PLANT NAMED 'VP004'**

(50) Latin Name: *Nephrolepis falcata*
Varietal Denomination: VP004

(75) Inventor: Nardo Zaias, Miami Beach, FL (US)

(73) Assignee: Magaly Zaias Fast, Coral Springs, FL (US)

( * ) Notice: Subject to any disclaimer, the term of this patent is extended or adjusted under 35 U.S.C. 154(b) by 201 days.

(21) Appl. No.: 10/877,840

(22) Filed: Jun. 25, 2004

(51) Int. Cl.
*A01H 9/00* (2006.01)

(52) U.S. Cl. ..... Plt./379
(58) Field of Classification Search ..... Plt./379
See application file for complete search history.

(56) References Cited

PUBLICATIONS http://www.oglesbytc.com/Culture/oglesby–nephrolepisfancy–frill.html.* http://www.oglesbytc.com/oglesby_details.asp?TF_ID=3024.*

* cited by examiner

*Primary Examiner*—Kent Bell
*Assistant Examiner*—W. C. Haas
(74) *Attorney, Agent, or Firm*—Mark P. Bourgeois

(57) ABSTRACT

A new cultivar of *Nephrolepis* plant named 'VP004' that is characterized by light green, narrow, short leaves and a compact habit. In combination, these traits set 'VP004' apart from other known existing varieties of *Nephrolepis*.

1 Drawing Sheet

Botanical designation: *Nephrolepis falcata.*
Variety denomination: 'VP004'.

BACKGROUND OF THE INVENTION

The present invention relates to a new and distinct cultivar of *Nephrolepis* plant botanically known as *Nephrolepis falcata* and hereinafter referred to by the cultivar name 'VP004'.

The new cultivar was discovered by the inventor in a cultivated area of Miami Beach, Fla. in October of 2001. 'VP004' was discovered as a naturally occurring whole-plant mutation of an unnamed plant of *Nephrolepis falcata* (not patented).

Asexual reproduction by division of the new cultivar 'VP004' was taken in October 2001 in Miami Beach, Fla. Since that time, under careful observation, the unique characteristics of the new cultivar have been uniform, stable and reproduced true to type in successive generations of asexual reproduction.

SUMMARY OF THE INVENTION

The following represent the distinguishing characteristics of the new *Nephrolepis* cultivar 'VP004'. These traits in combination distinguish 'VP004' as a new and distinct cultivar apart from other known existing varieties of *Nephrolepis.*

1. *Nephrolepis* 'VP004' exhibits narrow, short leaves.
2. *Nephrolepis* 'VP004' exhibits a compact habit.
3. *Nephrolepis* 'VP004' exhibits light green leaves.

The new cultivar 'VP004' is distinguishable from the unnamed parent *Nephrolepis* by the following characteristics:

1. 'VP004' has lighter green leaves.
2. 'VP004' has shorter leaves.
3. 'VP004' has a more compact habit.

4. 'VP004' has more narrow leaves.
5. 'VP004' has leaves that are less wavy.

BRIEF DESCRIPTION OF THE DRAWING

The accompanying photograph illustrates the distinguishing traits of *Nephrolepis* 'VP004'. The photograph shows an overall view of a 20 week old plant. The photographs were taken using conventional techniques and although colors may appear different from actual colors due to light reflectance it is as accurate as possible by conventional photographic techniques.

BOTANICAL DESCRIPTION OF THE PLANT

The following is a detailed description of the new *Nephrolepis* cultivar named 'VP004'. Data was collected in Renesse, Netherlands from 20 week old glass greenhouse grown plants. The time of year was Fall. The temperature ranged from 20–25° Centigrade during the day and 18–20° Centigrade at night. The light level was natural outdoor light. There were no photoperiodic treatments. Color determinations are in accordance with The Royal Horticultural Society Colour Chart 2001 edition, except where general color terms of ordinary dictionary significance are used. The growing requirements are similar to the species.

'VP004' has not been tested under all possible conditions and phenotypic differences may be observed with variations in environmental, climatic, and cultural conditions, however, without any variance in genotype.

Botanical classification: *Nephrolepis falcata.*
Use: Ornamental perennial.
Plant type: Potted Plant.
Parentage: 'VP004' was discovered as a naturally occurring mutation of an unnamed plant of *Nephrolepis falcata.*
Vigor: Medium.
Growth habit: Broad upright.

Growth rate: 5 cm. per month.
Plant shape: Globose.
Suitable container size: 5 liter.
Height: 50 cm. in height.
Width: 95 cm. in width.
Hardiness: USDA Zone 10.
Propagation: Tissue culture (by standard micro-propagation) or division.
Crop time: From propagation, approximately 20 weeks are required to produce a finished plant.
Time to initiate roots: 7 days at 25 degrees Centigrade.
Time to produce a rooted cutting or liner: 28 days. Rhizomes; Creeping, well branched and fibrous.
Stem: None, leaves grow directly from roots.
Frond:
*Arrangement.*—Alternate.
*Compound or single.*—Compound.
*Quantity.*—90 per plant.
*Length.*—78 cm. in length.
*Width.*—13.5 cm. in width.
Rachis:
*Diameter.*—3 mm.
*Color.*—137C.
*Pubescence.*—Strong, color 164C.
*Length to first pinnea.*—22.8 cm.
Pinnea:
*Quantity.*—56 per frond.
*Shape.*—Lanceolate, narrow.
*Apex.*—Apex is cleft into 2 lobes.
*Base.*—Acuminate.
*Length.*—9.6 cm. in length.
*Width.*—1.3 cm. in width.
*Pubescence.*—Slight, upper side, color 164B.
*Margin.*—Entire, slightly wavy.
*Vein pattern.*—Parallel.
*Young color* (*lower surface*).—143A.
*Young color* (*upper surface*).—Between 143A and 146A.
*Mature color* (*lower surface*).—137C.
*Mature color* (*upper surface*).—143AC.
*Vein color* (*lower surface*).—147A.
*Vein color* (*upper surface*).—147A.
*Texture.*—Smooth, glossy.
Reproductive organs: None observed, no spores observed.
Disease resistance: Has not been observed.

It is claimed:

1. A new and distinct variety of *Nephrolepis* plant named 'VP004' as described and illustrated.

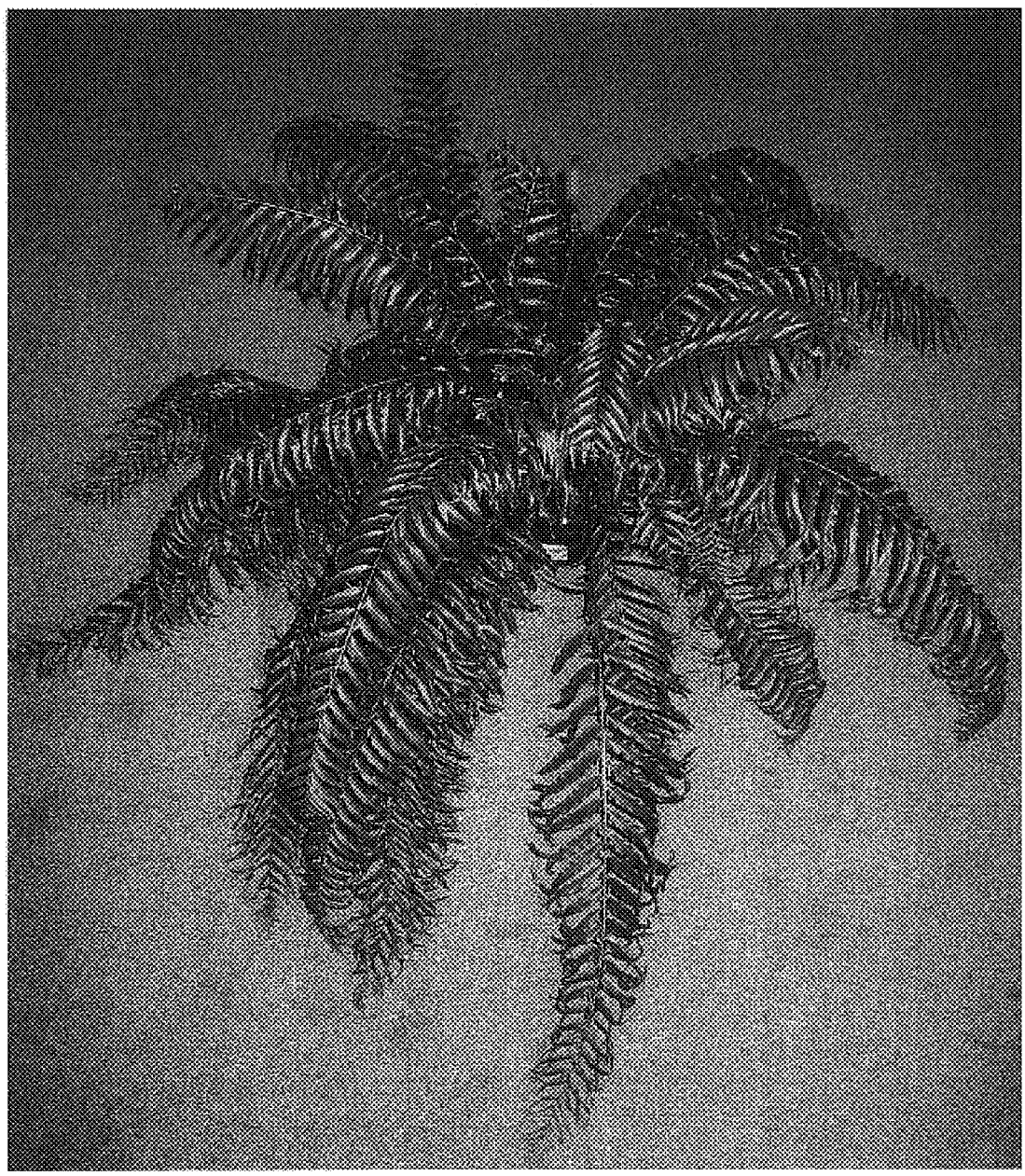

* * * * *